United States Patent [19]

Hanifl

[11] E Patent Number: Re. 33,413

[45] Reissued Date of Patent: Oct. 30, 1990

[54] SHARPS DISPOSAL SYSTEM

[75] Inventor: Paul H. Hanifl, Barrington, Ill.

[73] Assignee: Sage Products, Inc., Cary, Ill.

[21] Appl. No.: 445,367

[22] Filed: Dec. 4, 1989

Related U.S. Patent Documents

Reissue of:

[64] Patent No.: 4,715,498
Issued: Dec. 29, 1987
Appl. No.: 934,413
Filed: Nov. 24, 1986

[51] Int. Cl.[5] ..... B65F 1/16

[52] U.S. Cl. ..... 206/366

[58] Field of Search ..... 232/43.1, 43.2, 45, 232/47; 312/223, 211; 220/1 T; 206/366, 63.5

[56] References Cited

U.S. PATENT DOCUMENTS

| | | | |
|---|---|---|---|
| 3,322,477 | 5/1967 | Armijo | 232/43.2 |
| 3,981,436 | 9/1976 | Neal | 232/43.2 X |
| 4,315,592 | 2/1982 | Smith | 229/149 |
| 4,453,648 | 6/1984 | Harris et al. | 220/1 T X |
| 4,494,652 | 1/1985 | Nelson et al. | 206/63.5 X |
| 4,714,168 | 12/1987 | Johnson et al. | 206/366 X |

*Primary Examiner*—William I. Price
*Attorney, Agent, or Firm*—Lee, Mann, Smith, McWilliams & Sweeney

[57] ABSTRACT

A disposal system particularly adapted for hospital use comprising two portions. The first portion is composed of a hollow, outer enclosure adapted for wall-mounting and including an elongated slot inlet at the top with a barrier adjacent the slot for restricting access to the interior of the enclosure. The enclosure also includes a hinged access door for permitting insertion of the second portion of the invention, an inner container, therewithin. The inner container includes an inlet formed in registration with the slot when installed within the enclosure. The inner container includes a pivotal closure which may be locked in place when full in order to prevent access to the contents of the container.

25 Claims, 2 Drawing Sheets

SHARPS DISPOSAL SYSTEM

Matter enclosed in heavy brackets [ ] appears in the original patent but forms no part of this reissue specification; matter printed in italics indicates the additions made by reissue.

BACKGROUND OF THE INVENTION

This invention relates to disposal of contaminated items, and in particular to a disposal system for use in a hospital or similar environment where contaminated items must be collected and disposed of without creating a hazard for patients or hospital personnel.

In hospitals, clinics and similar institutions, contamination is of utmost concern. Disposable, single use patient-care products, which used to be the exception, are now the norm. Current guidelines of the U.S. Center for Disease Control require immediate disposal of hypodermic needles or other sharps at their site of use immediately following an injection.

Many different types of containers are available for sharps disposal, including many manufactured by Sage Products, Inc., the assignee of this application. Such containers are normally portable and provide somewhat limited protection against an individual's gaining access to sharps within the container. Improper reuse and possible contamination can ensue.

SUMMARY OF THE INVENTION

The invention provides a secure, readily-accessible system for disposal and comprises a hollow, outer enclosure and an inner, disposable container located within the outer enclosure. An elongated slot is provided at the top of the enclosure for permitting access to its interior. A barrier means is disposed adjacent the slot for restricting access to the interior of the enclosure, with at least a portion of the barrier comprising a constriction extending over the slot. The inner container includes an inlet in registration with the slot to allow disposal of contaminated items therewithin.

[Preferablky,] *Preferably* the constriction adjacent the slot of the outer enclosure comprises a raised cowl. Similarly, the inlet in the inner container includes a hood disposed within and generally conforming to the cowl when the inner container is installed within the outer enclosure. The inner container is also provided with a pivotal closure which is disposed within the inlet.

In order to inpede or prevent access to the interior of the inner container after it has been filled, the hood of the inner container includes means for locking the pivotal closure. In accordance with the preferred embodiment of the invention, the locking means comprises a plurality of catches within the hood, each catch including a stop means which engages the closure when the closure is pivoted in one direction past the stop means into the interior of the hood. The configuration of the stop means prevents pivoting of the closure in the opposite direction when the closure has been pivoted past one of the stop means.

It is preferred that the system include means for sensing the level of the contents within the inner [containere] *container*. In accordance with one form of the invention, in order to do so the pivotal [coosure] *closure* is provided with a sensing means which comprises a downwardly-depending leg extending from the closure into the inner container. In accordance with a second form of the invention, the inner container includes transparent windows at opposite sides thereof, and a visual detector, such as a photoelectric device, is installed adjacent the windows. Adequate filling of the container will be detected by the photoelectric device and the filled container can be removed from the enclosure and discarded.

The outer enclosure is provided with an access door in order to permit easy removal and insertion of the inner container into the outer enclosure. [Whilte] *While* it is preferred that the front side of the enclosure comprise the door, other configurations, such as hinging the top of the enclosure, will also provide an adequate access for removal of the inner container.

Not only does the barrier adjacent the slot include the cowl extending over the slot, but also preferably a raised shelf is formed at one longitudinal side of the slot. The shelf and the cowl define therebetween a limited opening in the outer enclosure so that a hand cannot inadvertently or advertently pass through the slot of the outer enclosure into the interior of the inner container.

BRIEF DESCRIPTION OF THE DRAWINGS

The invention is described in greater detail in the ensuing description of one example embodying the best mode of the invention, taken in conjunction with the drawings, in which.

DESCRIPTION OF AN EXAMPLE EMBODYING THE BEST MODE OF THE INVENTION

Figure 1:
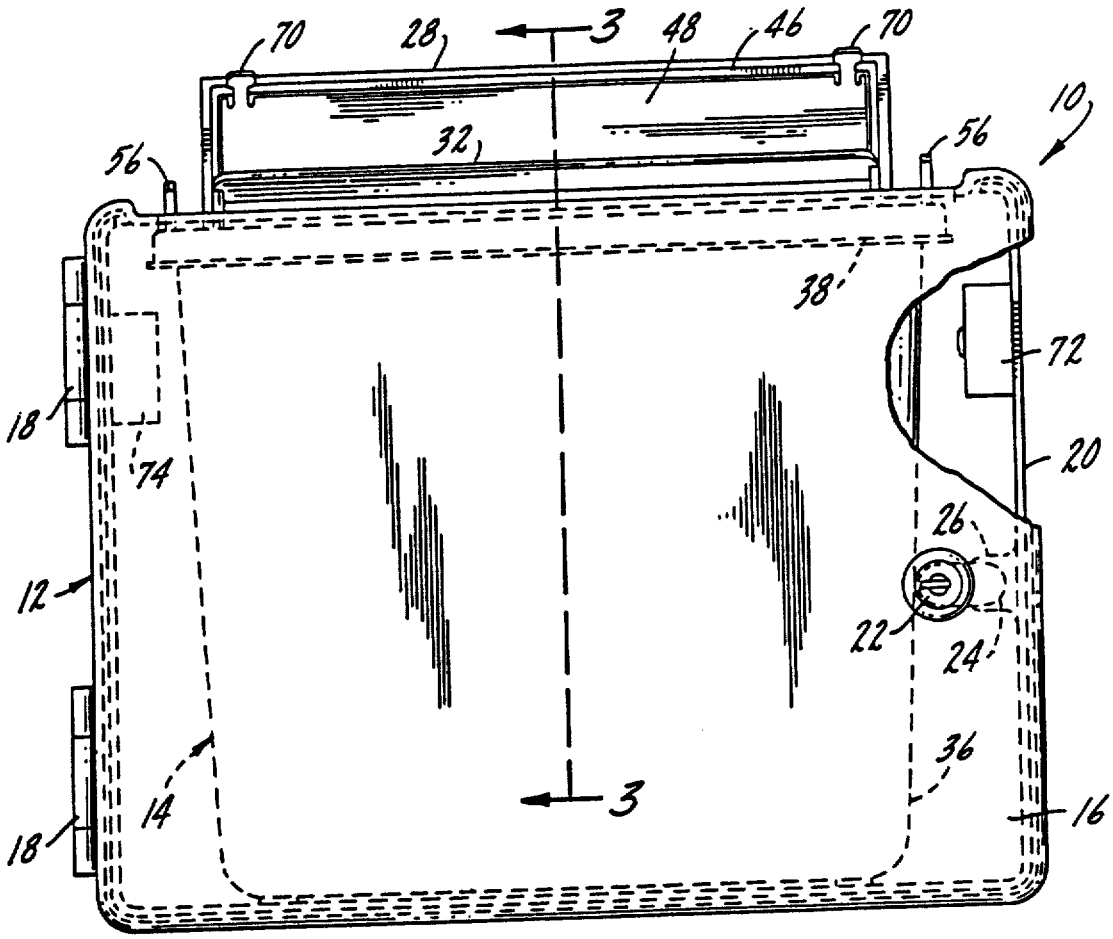
FIG. 1 is a front elevational view, with portions cut away, illustrating the sharps disposal system according to the invention.
Figure 2:
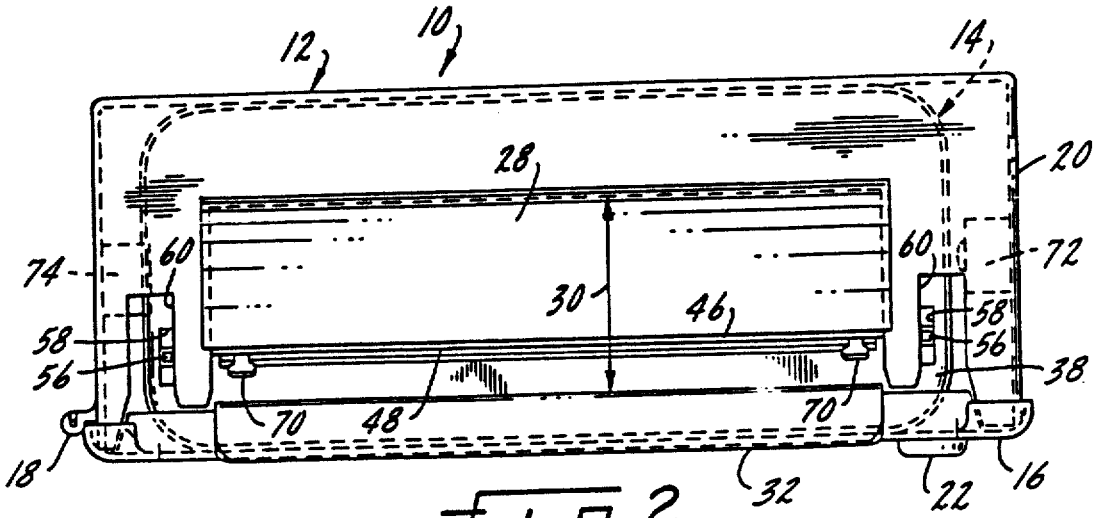
FIG. 2 is a top plan view thereof.

The Sharps Disposal System according to the invention is designated generally at 10 in the drawing figures. Primary components of the system 10 are a hollow, outer enclosure 12 and an inner container 14 shaped to be located within the outer enclosure 12.

Turning first to the outer enclosure 12, the enclosure 12 includes an access door 16 secured by hinges 18 onto the main body 20 of the enclosure 12. Opposite the hinges 18, the [doot] *door* 16 includes a lock 22 having a rotatable latch 24 which may be engaged behind a lug 26 extending inwardly from the body 20. When the latch 24 is rotated horizontally (as illustrated in FIG. 1), the latch 24 is engaged behind the lug 26, and the door 16 is locked. When the latch 24 is rotated to a vertical orientation, the leg 26 is no longer engaged, and the door 16 may be opened.

The main body 20 of the outer enclosure 12 includes a raised cowl 28 extending over a slot 30 in the top of the body 20. The cowl 28 constricts access to the slot 30 in order to restrict access to the interior of the outer enclosure 12, for reasons apparent below.

The door 16 also includes a raised shelf 32 extending along one side of the slot 30. The combination of the shelf 32 and the cowl 28 comprises a barrier restricting access to the interior of the outer enclosure 12. The realtive spacing of the shelf 32 and the cowl 28 defines a limited opening 34 which restricts access to the interior of the enclosure 12. As described in somewhat greater detail below, the opening 34 is dimensioned so that, in combination with the inner container 14 as described below, access is inhibited to the extent that it is difficult or impossible for an adult human hand to pass through the opening 34.

Figure 3:
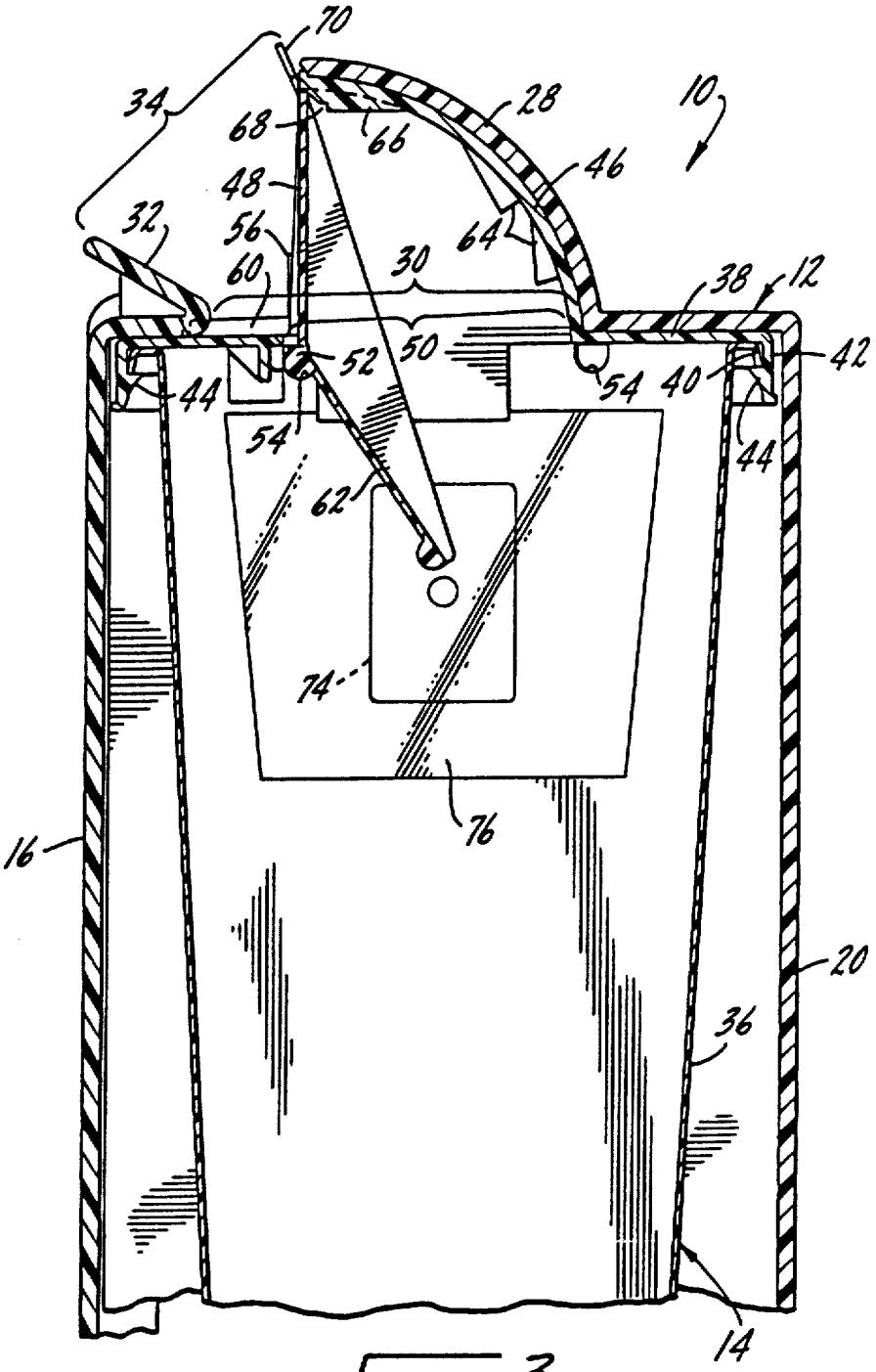
FIG. 3 is an enlarged cross-sectional view taken along lines 3—3 of FIG. 1.

The inner container 14 is composed of a receptacle 36 and a cover 38. The cover 38 is snap-fit to the receptacle 36. As best shown in FIG. 3, the receptacle 36 includes a peripheral, outwardly-extending flange 40 and the cover 38 includes a skirt 42 having an inwardly-extending lip 44 which snaps beneath the flange 40 when the cover 48 is placed on the receptacle 36.

The cover 38 of the container 14 includes [in] *an* integral hood 46 which, as best shown in FIG. 3, is shaped to conform to the cowl 28 when the container 14 is installed within the outer enclosure 12.

The container 14 includes a pivotal closure 48 installed within an inlet 50 formed in the cover 38. The closure 48 includes an integral rod 52 serving as the pivot for the closure 48, the rod extending beyond opposite ends of the closure 48 into opposite notches 54 formed in opposite sides of the receptacle 36. Tabs 56, extending from opposite ends of the rod 52, extend through apertures 58 in the cover 38 and further extend through indentations 60 formed in the top of the main body 20 of the outer enclosure 12.

The closure 48 also includes downwardly-depending leg 62 which extends into the interior of the inner container 14. The leg 62 serves two functions. With the orientation of the closure 48 as shown in the drawing figures, the leg 62 extends into the interior of the container 14 and will strike the contents therein if the receptacle 36 has been adequately filled. Thus, the leg 62 serves as a means for sensing the level of the contents within the container 14. Also, when the closure 48 is opened (pivoted to the left in FIG. 3), the leg 62 is raised substantially covering the inlet 50. Sharps or other items to be deposited within the inner container 14 are placed on the leg 62 when the closure 48 is opened, and when the closure 48 is returned to the closed orientation shown in FIG. 3, the sharps then drop within the container 14.

When the container 14 has been filled with sharps, it is preferably discarded. In order to secure the contents therewithin, a plurality of catches or locks 64 are formed in the interior of the hood 46. By applying pressure to the face of the closure 48, the closure is forced within the hood 46 and snaps past the first or both of the catches 64. Due to the configuration of the catches 64, the closure 48 may be pivoted past the catches toward the interior of the hood 46, but is prevented from returning. The contents of the container 14 are therefore secured.

If desired, the hood 46 may also include a temporary catch 66 for the closure 48. As shown in FIG. 3, the temporary catch 66 has a notch 68 formed to engage the top edge of the closure 48 to retain the closure in place.

As explained above, tabs 56 may be used to pivot the closure 48. If desired, the closure 48 may also be fitted with one or more additional tabs 70 which can be used in [palce] *place* of, in addition to, the tabs 58 for opening the closure 48.

The downwardly-depending leg 62 provides a tactile sensor for determining the level of the contents within the inner container 14. Instead of the leg 62 or in addition thereto, the system 10 may also include a photoelectric sensor 72 and transmitter 74 mounted in the interior of the outer enclosure 12 in registration with one another and aligned with opposite windows 76 formed in opposite side walls of the receptacle 36. When the level of the contents within the container 14 is adequate to inhibit a light beam between the transmitter 74 and detector 72, this condition may be transmitted to a light (not illustrated) or any other means of indicating that the inner container 14 has been filled and is ready for removal and replacement.

Both the outer enclosure 12 and the inner container 14 may be molded from a suitable plastic material. Because the inner container 14 is intended to be disposable, if it is formed of plastic, polypropelene or a similar plastic is most suitable since, when incinerated, the products of combustion are carbon dioxide and water. The outer enclosure 12 is preferably formed of a stiffer plastic which does not readily deform in use.

The purpose of the cowl 28 is twofold. As described above, the cowl 28 in combination with the shelf 32, define a limited opening to the interior of the enclosure 12. In addition, the cowl 28 stiffens the relatively flexible hood 46 so that a hand cannot be forced into the opening 34, deforming the opening and gaining access to the contents of the container 14.

The receptacle 36 is preferably symmetrical, and thus two notches 54 are formed in each of the opposite ends thereof to accomodate the cover 38 and closure 48 in any possible orientation.

While a primary and preferred embodiment of the invention has been illustrated and described above, various changes can be made to the invention without depating from the spirit thereof or scope of the following claims.

What is claimed is:

1. A disposal system comprising a. a hollow, outer enclosure, b. an elongated slot for permitting access to the interior of the outer enclosure, c. barrier means disposed adjacent said slot for restricting access to the interior of said outer enclosure, at least a portion of said barrier means comprising a constriction extending over said slot, and d. a removable inner container disposed within said outer enclosure, said inner container including an inlet in registration with [an] *and* no larger in dimension than said slot, said inlet extending into said slot.

2. A disposal system according to claim 1 in which said constriction comprises a cowl.

3. A disposal system according to claim 2 in which said inlet includes a hood on said inner container disposed within and generally conforming to said cowl.

4. A disposal system according to claim 3 including a pivotal closure disposed within said inlet, said hood including means for locking said closure to prevent access to the interior of said inner container.

5. A disposal system according to claim 4 in which said locking means comprises a plurality of catches within said hood, each catch including stop means engaging said closure when said closure is pivoted in one direction past said stop means into the interior of said hood, said stop means preventing pivoting of said closure in the opposite direction.

6. A disposal system according to claim 1 including means for sensing the level of contents within said inner container.

7. A disposal system according to claim 6 including a pivotal closure disposal within said inlet, and in which said sensing means comprises a downwardly-depending leg extending from said closure within said inner container.

8. A disposal system according to claim 6 in which said inner container includes transparent windows in opposite sides thereof, and said sensing means includes a visual detector adjacent said windows.

9. A disposal system according to claim 8 in which said visual detector comprises a photoelectric detector mounted in said outer enclosure adjacent one said window and a photoelectric transmitter mounted in said outer enclosure adjacent the other of said windows and in registration with said photoelectric detector.

10. A disposal system according to claim 1 including means permitting removal of said inner container from said outer enclosure.

11. A disposal system according to claim 10 in which said removal means comprises an access door in said outer enclosure.

12. A disposal system according to claim 1 in which said barrier means includes a raised shelf at one longitudinal side of said slot, and said constriction comprises a cowl extending from the opposite longitudinal side of said slot, said shelf and cowl defining therebetween a limited opening to said outer enclosure.

13. A disposal system comprising a. a hollow, outer enclosure, b. a slot in the top of said outer enclosure for permitting access to the interior of said outer enclosure, c. barrier means disposed adjacent said slot for restricting access to the interior of said outer enclosure, said barrier means including a cowl extending above and over said slot, d. an inner container disposed within said outer enclosure, said inner container having an inlet in alignment with and no larger in dimension than said slot, said inlet extending into said slot, and e. means permitting removal of said inner container from said outer enclosure.

14. A disposal system according to claim 13 in which said inlet includes a hood on said inner container disposed within and generally conforming to said cowl.

15. A disposal system according to claim 13 including a pivotal closure disposed within said inlet, said inner container including means for locking said closure to prevent access to the interior of said inner container.

16. A disposal system according to claim 13 in which said removal means comprises an access door in said outer enclosure.

17. A disposal system according to claim 13 in which said barrier means includes a raised shelf at one longitudinal side of said slot, and said cowl extends from the opposite longitudinal side of said slot, said shelf and said cowl defining therebetween a limited opening to said outer enclosure.

18. A disposal system comprising a. a hollow, outer enclosure, b. a slot in the top of said outer enclosure for permitting access to the interior of said outer enclosure, c. barrier means disposed adjacent said slot for restricting access to the interior of said outer enclosure, said barrier means including a cowl extending above and over said slot, d. an inner container disposed within said outer enclosure, said inner container having an inlet in alignment with said slot, said inlet including a hood disposed within and generally conforming to said cowl, and e. means permitting removal of said inner container from said outer enclosure.

19. A disposal system according to claim 19 including a pivotal closure disposed within said inlet, said hood including means for locking said closure to prevent access to the interior of said inner container.

20. A disposal system according to claim 19 in which said locking means comprises a plurality of catches within said hood, each catch including stop means engaging said closure when said closure is pivoted in one direction past said stop means into the interior of said hood, said stop means preventing pivoting of said closure in the opposite direction.

21. A disposal system according to claim 18 in which said barrier means includes a raised shelf at one longitudinal side of said slot, and said cowl extends from the opposite longitudinal side of said slot, said shelf and said cowl defining therebetween a limited opening to said outer enclosure.

*22. A disposal system comprising*

*a. a hollow, outer enclosure,*

*b. an elongated slot for permitting access to the interior of the outer enclosure,*

*c. barrier means disposed adjacent said slot for restricting access to the interior of said outer enclosure, at least a portion of said barrier means comprising a constriction extending over said slot, and*

*d. a removable inner container disposed within said outer enclosure, said inner container including an inlet in registration with said slot, said inlet including means for cooperating with said constriction for restricting access to the interior of said inner container.*

*23. A disposal system according to claim 22 in which said means for cooperating comprises a further barrier extending across said inlet.*

*24. A disposal system according to claim 23 in which said further barrier includes a hood on said inner container.*

*25. A disposal container according to claim 24 in which said constriction comprises a cowl, and said hood is disposed within and generally conforming to said cowl.*

* * * * *